United States Patent
Neven (10) Patent No.: US 8,510,166 B2
(45) Date of Patent: Aug. 13, 2013

(54) GAZE TRACKING SYSTEM

(75) Inventor: Hartmut Neven, Malibu, CA (US)

(73) Assignee: Google Inc., Mountain View, CA (US)

( * ) Notice: Subject to any disclaimer, the term of this patent is extended or adjusted under 35 U.S.C. 154(b) by 153 days.

(21) Appl. No.: 13/105,701

(22) Filed: May 11, 2011

(65) Prior Publication Data

US 2012/0290401 A1    Nov. 15, 2012

(51) Int. Cl.
*G06Q 30/00*    (2012.01)

(52) U.S. Cl.
USPC ..................... 705/14.68; 705/14.69

(58) Field of Classification Search
USPC ....................................................... 705/14.68
See application file for complete search history.

(56) References Cited

U.S. PATENT DOCUMENTS

| | | | |
|---|---|---|---|
| 4,711,512 A | 12/1987 | Upatnieks | |
| 4,852,988 A | 8/1989 | Velez et al. | |
| 4,972,504 A * | 11/1990 | Daniel et al. | 705/7.29 |
| 5,076,664 A | 12/1991 | Migozzi | |
| 5,315,093 A * | 5/1994 | Stewart | 235/381 |
| 5,331,544 A * | 7/1994 | Lu et al. | 705/7.29 |
| 6,011,578 A * | 1/2000 | Shatto et al. | 725/14 |
| 6,307,526 B1 | 10/2001 | Mann | |
| 6,393,136 B1 * | 5/2002 | Amir et al. | 382/103 |
| 6,526,156 B1 * | 2/2003 | Black et al. | 382/103 |
| 6,539,100 B1 * | 3/2003 | Amir et al. | 382/117 |
| 6,577,329 B1 * | 6/2003 | Flickner et al. | 715/774 |
| 6,608,615 B1 | 8/2003 | Martins | |
| 6,661,907 B2 * | 12/2003 | Ho et al. | 382/118 |
| 6,690,516 B2 | 2/2004 | Aritake et al. | |
| 6,707,933 B1 * | 3/2004 | Mariani et al. | 382/118 |
| 6,741,756 B1 * | 5/2004 | Toyama et al. | 382/291 |
| 6,772,129 B2 * | 8/2004 | Alvarez et al. | 705/14.41 |
| 6,973,201 B1 * | 12/2005 | Colmenarez et al. | 382/103 |
| 7,035,456 B2 * | 4/2006 | Lestideau | 382/164 |
| 7,043,056 B2 * | 5/2006 | Edwards et al. | 382/103 |
| 7,046,826 B2 * | 5/2006 | Toyama | 382/103 |
| 7,092,971 B2 * | 8/2006 | Idei et al. | 1/1 |
| 7,120,880 B1 * | 10/2006 | Dryer et al. | 715/863 |
| 7,558,922 B2 * | 7/2009 | Murase | 711/137 |
| 7,643,658 B2 * | 1/2010 | Kilner et al. | 382/118 |
| 7,657,062 B2 | 2/2010 | Pilu | |
| 7,736,000 B2 | 6/2010 | Enriquez et al. | |
| 7,769,632 B2 * | 8/2010 | Giraud et al. | 705/14.4 |

(Continued)

OTHER PUBLICATIONS

Babcock, J.S. & Pelz, J.B., "Building a lightweight eyetracking headgear", Proceedings of the 2004 Symposium on Eye Tracking Research & Applications; Rochester Institute of Technology. 2004, pp. 109-113.

(Continued)

*Primary Examiner* — Jacob C. Coppola
(74) *Attorney, Agent, or Firm* — Blakely Sokoloff Taylor & Zafman LLP (57) ABSTRACT

A gaze tracking technique is implemented with a head mounted gaze tracking device that communicates with a server. The server receives scene images from the head mounted gaze tracking device which captures external scenes viewed by a user wearing the head mounted device. The server also receives gaze direction information from the head mounted gaze tracking device. The gaze direction information indicates where in the external scenes the user was gazing when viewing the external scenes. An image recognition algorithm is executed on the scene images to identify items within the external scenes viewed by the user. A gazing log tracking the identified items viewed by the user is generated.

25 Claims, 6 Drawing Sheets

(56) References Cited

U.S. PATENT DOCUMENTS

| | | |
|---|---|---|
| 2002/0010623 A1* | 1/2002 | Mccollom et al. .............. 705/14 |
| 2002/0102024 A1* | 8/2002 | Jones et al. .................. 382/225 |
| 2002/0116265 A1* | 8/2002 | Hernandez ...................... 705/14 |
| 2002/0159627 A1* | 10/2002 | Schneiderman et al. ..... 382/154 |
| 2003/0098954 A1* | 5/2003 | Amir et al. .................... 351/210 |
| 2003/0107649 A1* | 6/2003 | Flickner et al. .............. 348/150 |
| 2003/0161500 A1* | 8/2003 | Blake et al. ................... 382/103 |
| 2004/0100567 A1 | 5/2004 | Miller et al. |
| 2004/0240708 A1* | 12/2004 | Hu et al. ....................... 382/103 |
| 2005/0180626 A1* | 8/2005 | Moon et al. ................... 382/159 |
| 2005/0200476 A1* | 9/2005 | Forr et al. ................. 340/539.13 |
| 2005/0203798 A1* | 9/2005 | Jensen et al. ..................... 705/14 |
| 2005/0265581 A1* | 12/2005 | Porter et al. .................. 382/103 |
| 2006/0041480 A1* | 2/2006 | Briggs ............................. 705/14 |
| 2006/0212658 A1* | 9/2006 | Hrle et al. ..................... 711/137 |
| 2007/0150450 A1* | 6/2007 | Murase ............................. 707/3 |
| 2008/0147488 A1 | 6/2008 | Tunick et al. |
| 2010/0103075 A1 | 4/2010 | Kalaboukis et al. |
| 2010/0287175 A1* | 11/2010 | Beaudreau et al. ........... 707/759 |
| 2010/0318538 A1* | 12/2010 | Wyman et al. ................ 707/759 |
| 2011/0034176 A1 | 2/2011 | Lord et al. |
| 2011/0208593 A1* | 8/2011 | Nishida et al. ............. 705/14.68 |
| 2011/0213664 A1 | 9/2011 | Osterhout et al. |
| 2012/0106857 A1* | 5/2012 | Schneiderman ............. 382/224 |

OTHER PUBLICATIONS

Li, D., Babcock, J., and Parkhurst, D.J., "openEyes: a low-cost head-mounted eye-tracking solution", Proceedings of the 2006 Symposium on Eye Tracking Research & Applications, The Human Computer Interaction Program; Iowa State University, Ames, Iowa. 7 pages, 2006.

Applied Science Laboratories, "H6HS Head Mounted Eye Tracking System," Innovations in Eye Tracking, 2009, 2 pages.

PCT/US2012/035275; International Search Report and Written Opinion, mailed Aug. 13, 2012, 15 pages.

* cited by examiner

GAZE TRACKING SYSTEM

TECHNICAL FIELD

This disclosure relates generally to client-server computer processing techniques, and in particular but not exclusively, relates to a gaze tracking system.

BACKGROUND INFORMATION

Eye tracking systems use cameras to measure eye movement/position to determine the point of gaze (i.e., where you are looking). Eye trackers have been used in human computer interaction systems, psychology, and other research field endeavors. There are a number of techniques to measure eye movement including video images from which eye position can be determined. To date, eye tracking systems have mostly been limited to research endeavors because of the intrusiveness, high cost, and reliability of these systems. A technique and system that can provide a reliable, low cost, and unobtrusive, eye tracking system could have a variety of useful everyday applications.

SUMMARY

Implementations of techniques, apparatuses, and systems are provided for a gaze tracking system. In one aspect, a method includes: receiving scene images from a head mounted gaze tracking device capturing external scenes viewed by a user wearing the head mounted device, the scene images received at a server via a network; receiving gaze direction information from the head mounted gaze tracking device along with the scene images, the gaze direction information indicating where in the external scenes the user was gazing when viewing the external scenes, the gaze direction information received at the server via the network; executing an image recognition algorithm on the scene images to identify items within the external scenes viewed by the user; and generating a gazing log tracking the identified items viewed by the user.

In another aspect, a method includes: capturing a scene image of an external scene that includes a plurality of items perceived by a user, wherein the scene image is captured in real-time with a forward facing scene camera disposed on eyeglasses worn by the user; capturing an eye image of an eye of the user in real-time while the user is perceiving the external scene through the eyeglasses, wherein the eye image is captured with a gaze tracking camera disposed on the eyeglasses; generating gaze direction information in real-time based upon the eye image; and identifying one of the plurality of items within the external scene at which the user is gazing based at least in part upon the gaze direction information.

In another aspect, a head mounted gaze tracking apparatus includes: a glasses frame including side-arms for engaging ears of a user; lens elements mounted to the glasses frame, the lens elements being at least partially transparent so that the user can perceive an external scene through the lens elements and at least partially reflective; a scene camera mounted to the glasses frame and oriented forward facing to capture a scene image of the external scene; a gaze tracking camera mounted to the glasses frame and positioned to capture an eye image of an eye of the user as a reflection off of one of the lens elements; and a processing system communicatively coupled to the scene camera and the gaze tracking camera to receive and correlate the eye image to the scene image to track whom or what the user views.

These and other aspects and embodiments are described in detail in the drawings, the description, and the claims.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of a system, apparatus, and methods for a gaze tracking system are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
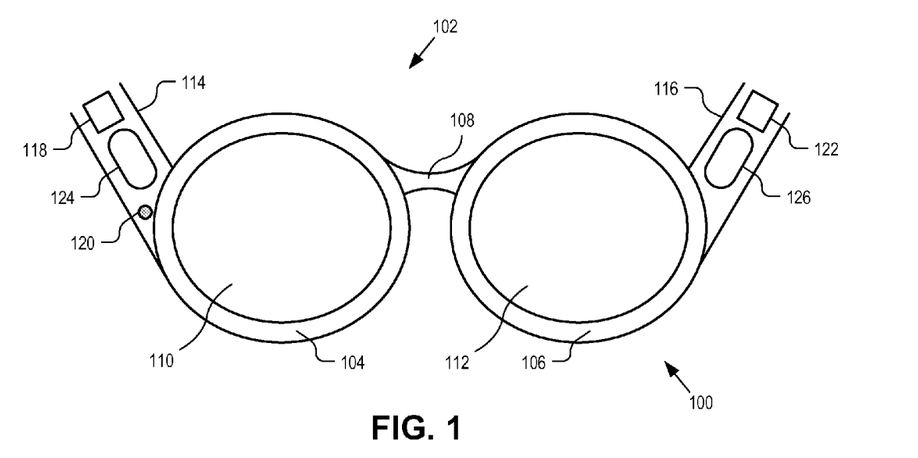
FIG. 1 illustrates an example head mounted gaze tracking device, in accordance with an embodiment.
Figure 2:
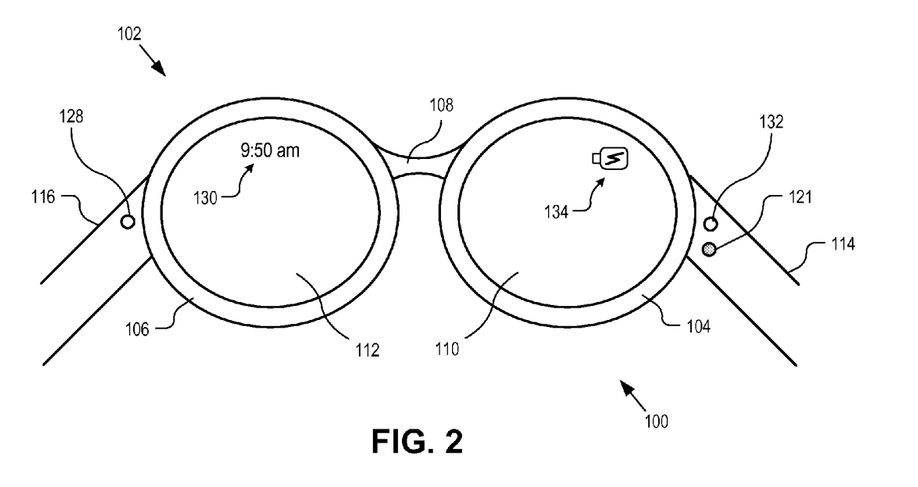
FIG. 2 illustrates an alternative view of the device of FIG. 1, in accordance with an embodiment.

FIGS. 1 and 2 illustrate an example head mounted gaze tracking device 100, in accordance with an embodiment. The device 100 is shown in the form of a wearable computing device. While FIG. 1 illustrates eyeglasses 102 as an example of a head mounted gaze tracking device, other types of wearable computing devices could additionally or alternatively be used. As illustrated in FIG. 1, the eyeglasses 102 comprise frame elements including lens-frames 104 and 106 and a center frame support (or nose bridge) 108, lens elements 110 and 112, and side-arms 114 and 116. The center frame support 108 and the side-arms 114 and 116 are configured to secure the eyeglasses 102 to a user's face via a user's nose and ears, respectively. Each of the frame elements 104, 106, and 108 and the side-arms 114 and 116 may be formed of a solid structure of plastic or metal, or may be formed of a hollow structure of similar material so as to allow wiring and component interconnects to be internally routed through the eyeglasses 102. Each of the lens elements 110 and 112 is sufficiently transparent (e.g., at least partially transparent) to allow the user to see through the lens element to view the external scene of their environment. Each of the lens elements 110 and 112 may also be formed of any material that can suitably display a projected image or graphic. Combining these two features of the lens elements can facilitate an augmented reality or heads-up display where the projected image or graphic is superimposed over a real-world view as perceived by the user through the lens elements.

The side-arms 114 and 116 each extend away from the frame elements 104 and 106, respectively, and engage a user's ears to secure the eyeglasses 102 to the user. The side-arms 114 and 116 may further secure the eyeglasses 102 to the user by extending around a rear portion of the user's head. Additionally or alternatively, for example, device 100 may connect to or be affixed within a head-mounted helmet structure. Other possibilities exist as well.

The device 100 may also include an on-board computing system 118, a scene camera (e.g., video camera) 120, a gaze tracking camera 121, a sensor 122, and finger-operable touch pads 124, 126. The on-board computing system 118 is shown to be positioned on the side-arm 114 of the eyeglasses 102; however, the on-board computing system 118 may be provided on other parts of the eyeglasses 102. The on-board computing system 118 may include a processor and memory, for example. The on-board computing system 118 may be configured to receive and analyze data from the scene camera 120 and the finger-operable touch pads 124, 126 (and possibly from other sensory devices, user interfaces, or both) and generate images for output from the lens elements 110 and 112 to the user's eyes.

The scene camera 120 is shown to be forward facing and positioned on the extending side-arm 114 of the eyeglasses 102; however, the scene camera 120 may be provided on other parts of the eyeglasses 102 (e.g., frame elements 104, 106, or 108). The scene camera 120 may be configured to capture images at various resolutions or at different frame rates of the external scene viewed by the user through lens elements 110 and 112. Many video cameras with a small form-factor, such as those used in cell phones or webcams, for example, may be integrated into device 100 to implement scene camera 120. Although FIG. 1 illustrates just one scene camera 120, more scene cameras may be used, and each may be configured to capture the same view, or to capture different views. For example, the scene camera 120 may be forward facing to capture at least a portion of the real-world view perceived by the user. This forward facing image captured by the scene camera 120 may then be used to implement gaze tracking as discussed below or even to generate an augmented reality where computer generated images appear to interact with the external scene or real-world view perceived by the user.

Gazing tracking camera 121 is positioned to acquire eye images (e.g., video images) of the user's eye. These eye images can then be analyzed to generate gaze direction information, which can be used to determine the user's gazing direction. The gaze direction information can be correlated to the scene images acquired by scene camera 120 to determine at what item (e.g., person, place, or thing) the user was directly looking at when viewing the external scene through lens elements 110 and 112. The illustrated embodiment of gazing tracking camera 121 is disposed on the inside of side-arm 114 and faces substantially forward to record the eye images via a reflection off of the lens element 110. Alternatively, gazing tracking camera 121 may be positioned sufficiently forward on side-arm 114 to be angled backward to directly face and acquire direct images (e.g., without reflections) of the user's eye from a peripheral vantage point. Although FIGS. 1 and 2 illustrate a single gaze tracking camera 121 positioned on the right side of eyeglasses 102, other embodiments may include multiple gaze tracking cameras (e.g., one to record video images of each eye) having other positions (e.g., positioned on any of frame elements 104, 106, 108, 114, and 116).

Scene camera 120 and gaze tracking camera 121 may be operated to acquire continuous real-time images that are time keyed to each other as the user views the external scene. In one embodiment, on-board computer system 118 is coupled to analyze the eye images acquired by gaze tracking camera 121 and the scene images acquired by scene camera 120 in real-time, to generate gaze direction information in real-time, to correlate the gaze direction information to the scene images in real-time, and to "lock on" and track an item in the scene images which corresponds to the item at which the user is currently gazing or staring.

The sensor 122 is shown mounted on the side-arm 116 of the eyeglasses 102; however, the sensor 122 may be provided on other parts of the eyeglasses 102. The sensor 122 may include one or more of a gyroscope or an accelerometer, for example. Other sensing devices may be included within the sensor 122 or other sensing functions may be performed by the sensor 122.

The finger-operable touch pads 124, 126 are shown mounted on the side-arms 114, 116 of the eyeglasses 102. Each of finger-operable touch pads 124, 126 may be used by a user to input commands. The finger-operable touch pads 124, 126 may sense at least one of a position and a movement of a finger via capacitive sensing, resistance sensing, or a surface acoustic wave process, among other possibilities. The finger-operable touch pads 124, 126 may be capable of sensing finger movement in a direction parallel or planar to the pad surface, in a direction normal to the pad surface, or both, and may also be capable of sensing a level of pressure applied. The finger-operable touch pads 124, 126 may be formed of one or more translucent or transparent insulating layers and one or more translucent or transparent conducting layers. Edges of the finger-operable touch pads 124, 126 may be formed to have a raised, indented, or roughened surface, so as to provide tactile feedback to a user when the user's finger reaches the edge of the finger-operable touch pads 124, 126. Each of the finger-operable touch pads 124, 126 may be operated independently, and may provide a different function.

FIG. 2 illustrates an alternate view of the device 100 of FIG. 1. As shown in FIG. 2, the lens elements 110 and 112 may act as display elements. The eyeglasses 102 may include a first projector 128 coupled to an inside surface of the side-arm 116 and configured to project a display 130 onto an inside surface of the lens element 112. Additionally or alternatively, a second projector 132 may be coupled to an inside surface of the side-arm 114 and configured to project a display 134 onto an inside surface of the lens element 110.

The lens elements 110 and 112 may act as a combiner in a light projection system and may include a coating that reflects the light projected onto them from the projectors 128 and 132. In some embodiments, a special coating may not be used (e.g., when the projectors 128 and 132 are scanning laser devices).

In alternative embodiments, other types of display elements may also be used. For example, the lens elements 110, 112 themselves may include: a transparent or semi-transparent matrix display, such as an electroluminescent display or a liquid crystal display, one or more waveguides for delivering an image to the user's eyes, or other optical elements capable of delivering an in focus near-to-eye image to the user. A corresponding display driver may be disposed within the frame elements 104 and 106 for driving such a matrix display. Alternatively or additionally, a laser or LED source and scanning system could be used to draw a raster display directly onto the retina of one or more of the user's eyes. Other possibilities exist as well.

Figure 3:
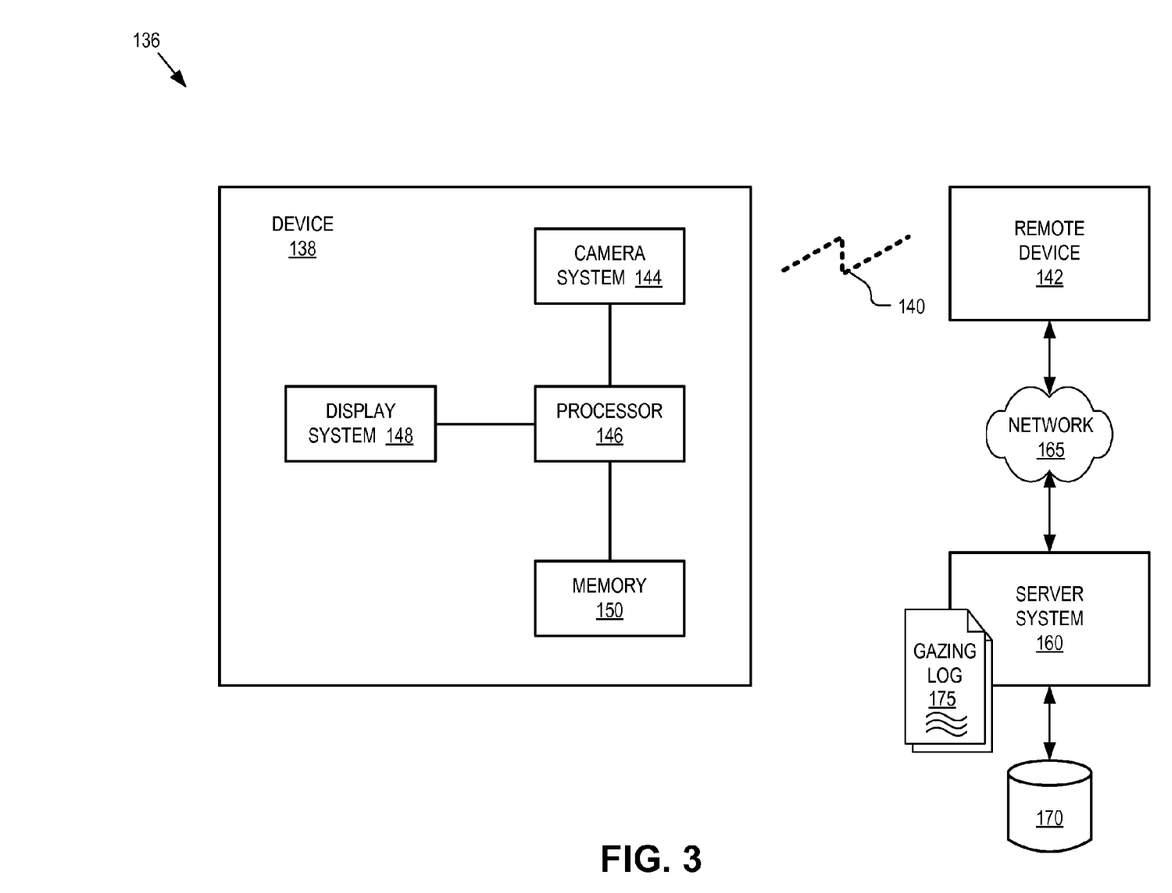
FIG. 3 is a functional block diagram illustrating a processing system infrastructure, in accordance with an embodiment.

FIG. 3 illustrates a functional block diagram of a computer network infrastructure 300, in accordance with an embodiment. In one system 136, a device 138 communicates using a communication link 140 (e.g., a wired or wireless connection) to a remote device 142. The device 138 may be any type of device that can acquire images, transmit the images, receive data, and optional display information corresponding to or associated with the data. For example, the device 138 may be a head mounted display system, such as the eyeglasses 102 described with reference to FIGS. 1 and 2.

Thus, the device 138 may include a processor 146, a display system 148, a camera system 144, and memory 150. The display system 148 may be, for example, an optical see-through display, an optical see-around display, or a video see-through display. Camera system 144 may include, for example, a forward facing video camera system (e.g., scene camera) to acquire external scene (real-world) images and a gaze tracking camera system to acquire eye images. The processor 146 may receive data from camera system 144, pre-process the data, buffer the data in memory 150, and/or transmit the data to remote device 142. The processor 146 may also receive data from the remote device 142, and configure the data for display on the display 148. The processor 146 may be any type of processor, such as a micro-processor or a digital signal processor, for example.

The device 138 may further include on-board data storage, such as memory 150 coupled to the processor 146. The memory 150 may store software that can be accessed and executed by the processor 146, for example.

The remote device 142 may be any type of computing device or transmitter including a laptop computer, a mobile telephone, etc., that is configured to communicate with the device 138. The remote device 142 and the device 138 may contain hardware to enable the communication link 140, such as processors, transmitters, receivers, antennas, etc. In FIG. 3, the communication link 140 is illustrated as a wireless connection; however, wired connections may also be used. For example, the communication link 140 may be a wired link via a serial bus such as a universal serial bus or a parallel bus. A wired connection may be a proprietary connection as well. The communication link 140 may also be a wireless connection using, e.g., Bluetooth® radio technology, communication protocols described in IEEE 802.11 (including any IEEE 802.11 revisions), Cellular technology (such as GSM, CDMA, UMTS, EVDO, WiMAX, or LTE), or Zigbee® technology, among other possibilities.

The remote device 142 may access the Internet or World Wide Web to gain access to various types of communication services (e.g., social-networking, photo sharing, address book, etc.). For example, remote device 142 may access server system 160 via network 165. Network 165 may represent a local area network, a wide area network, metro area network, the web, or the Internet. Server system 160 may provide various processing services, such as, visual search capabilities, web search capabilities, database services, access to social-networking services, or otherwise. For example, data received at server system 160 routed from device 138 may be tracked and logged into a database 170.

In one embodiment, device 138 is a head mounted gaze tracking device, remote device 142 is a smart phone, and server system 160 provides real-time logging and image searching of data images acquired by device 138. In this example, remote device 138 may be kept in the pocket of the user wearing device 138 and running application software for interacting with device 138 via a wireless Bluetooth link. The application software may receive scene images and gaze direction information from device 138, pre-process the data and forward the data onto server 160. Remote device 142 may transmit the data via a WiFi link or cellular network data link to server system 160. Upon receipt, server system 160 may process the data, provide response data, and even log the received data into database 170 on a per user basis. Thus, server system 160 may communication with a plurality of devices 138. Although FIG. 3 illustrates device 138 communicated with server system 160 using remote device 142 as an intermediary, in other embodiments, remote device 142 may be by-passed if device 138 has its own access to network 165 (e.g., incorporates a WiFi or cellular network transceiver).

Figure 4:
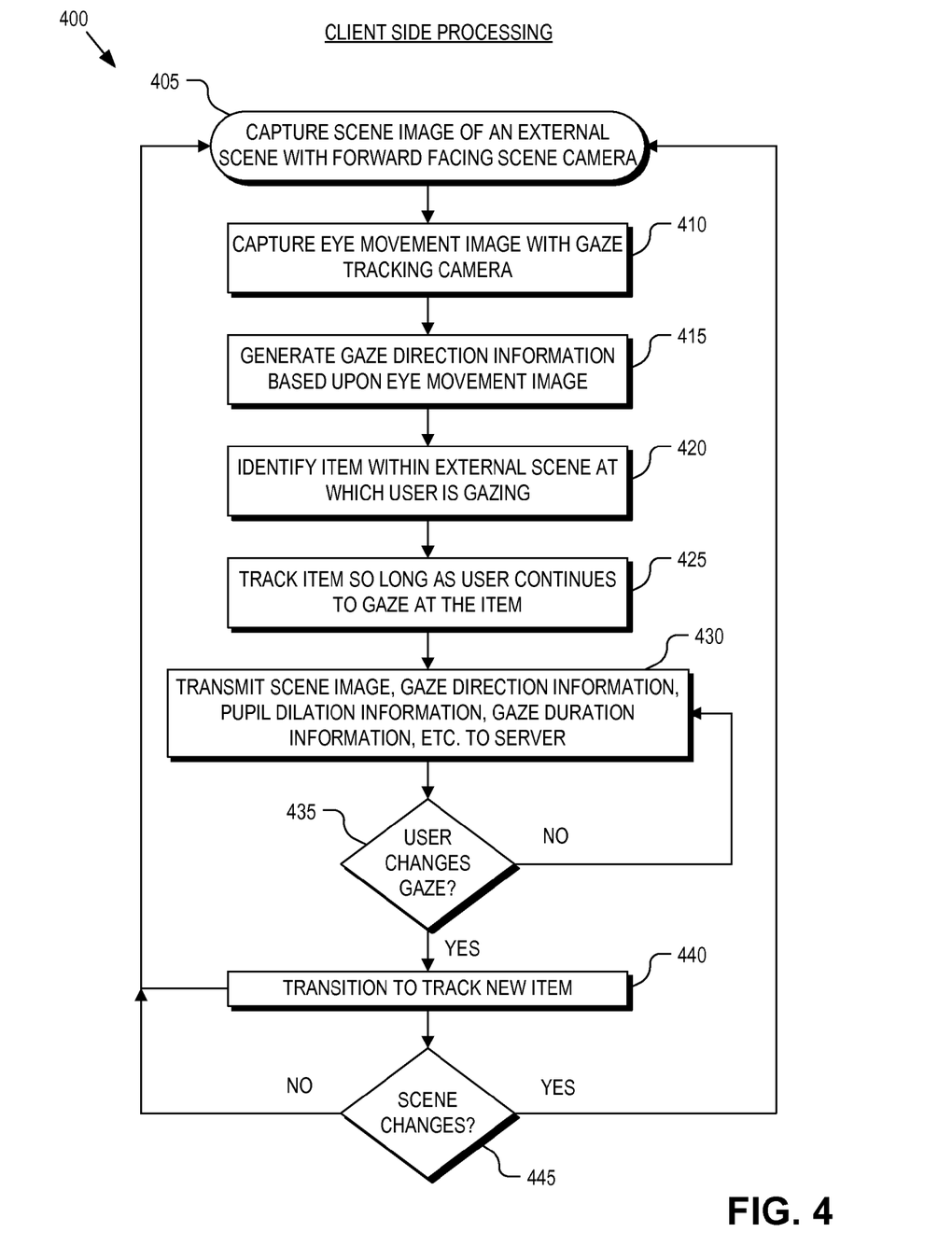
FIG. 4 is a flow chart illustrating client side processing for gaze tracking, in accordance with an embodiment.

FIG. 4 is a flow chart illustrating a client side process 400 for gaze tracking, in accordance with an embodiment. Process 400 may be executed by device 138 illustrated in FIG. 3 or head mounted gaze tracking device 100 illustrated in FIGS. 1 and 2. The order in which some or all of the process blocks appear in process 400 should not be deemed limiting. Rather, one of ordinary skill in the art having the benefit of the present disclosure will understand that some of the process blocks may be executed in a variety of orders not illustrated or even in parallel.

In a process block 405, scene camera 120 acquires a scene image of an external scene of the real-world as viewed by the user wearing device 100. In one embodiment, a scene image is a single frame of a continuous video steam of scene images. The scene images may be captured using a variety of different standardized imaging codecs (e.g., MPEG, MPEG-4, series of JPEG images, etc.), or a proprietary imaging protocol. The scene image may be an image of anything viewed by the user and thus may include a plurality of items. For example, if the user is sitting at an office desk, the user's external scene may include various items such as a keyboard, a mouse, a desk top computer, a monitor, a number of books, one or more pictures on the wall, etc. Images of these items would thus be included within the scene image acquired by the forward facing scene camera 120. The scene images may be acquired continuously in real-time recording everything viewed by the user.

In a process block 410, gaze tracking camera 121 acquires an eye image of an eye of the user in real-time while the user is perceiving the external scene through lens elements 110 and 112. Gaze tracking camera 121 acquires the eye images contemporaneously with scene camera 120 acquiring the scene images and the two image streams are time keyed or synchronized with each other. The eye images include an image of the user's eye, which may be acquired as a direct image or acquired via a reflection off of one or more of lens elements 110 and 112. The scene images and the eye images may both be temporarily buffered into memory 150 before one or both are transmitted to server system 160. In some embodiments, the scene and eye images may be pre-processed at device 138 by processor 146 (or on-board computing system 118) before being exported.

In a process block 415, the eye image is analyzed to generate gaze direction information. In one embodiment, the gaze direction information may be generated based upon the pupil location within the eye image. For example, if the pupil is located in the center of the eye image, this position may correlate to a straight forward gazing direction. Alternatively, if the pupil is located at the center bottom of the eye image, this position may correlate to a straight down gazing direction. Prior to operating, the user may be asked to execute a calibration test where the user is instructed to look in various directions or at various objects or virtual objects displayed in lens elements 110 and 112. During the calibration, the pupil location within each eye image may then be calibrated to the corresponding items captured in the scene images.

In a process block 420, the gazing information extracted from the eye images is used to determine which item within the external scene the user is staring or gazing directly at. For example, a gazing direction can be inferred from the gazing information, which is then used to select a localized region within the corresponding captured scene image. This localized region can then be analyzed using other techniques to lock onto a particular item at which the user may be gazing at. Various techniques such as searching for geometric shapes, contrast points, etc. may be used to determine which item within the localized region of the scene image the user is gazing at.

In a process block 425, once a trackable item is identified, it will continue to be tracked by on-board computing system 118 so long as the user continues to gaze in the item's direction or the item passes out of view or is not longer sufficiently discernable within successive scene images to be trackable. Item tracking may be a background processing task that executes without the user's knowledge or at least without a discernable tracking queue being presented to the user. In alternative embodiments, the user may be presented with a visual queue painted over the item in the user's real-world view (e.g., box, highlighted, etc) using projectors 128 and/or 132.

In a process block 430, device 100 (or device 138) transmits information to server system 160 so that a gazing log 175 can be generated for the particular user. Gazing log 175 can operate as a historical log of what, when, how long, and even how intensely the user looked at various items over the course of a viewing session, a day, a week, or even months and years. The information transmitted to server system 160 may include the scene images (or parsed/compressed versions thereof), the eye images, and/or the gazing information. In addition to the gazing information, pupil dilation information from which user emotion while viewing a particular item can be inferred may also be collected and transmitted to server system 160. In one embodiment, the pre-processed gazing information is transmitted to server system 160 instead of the eye images themselves. Similarly, in some embodiments, not all scene images acquired by scene camera 120 are transmitted. Rather, various bandwidth saving techniques may be used such as transmitting every Nth scene image, transmitting a key frame with subsequent change vectors, transmitting only the localized portion of the scene image identified from the gaze direction information, transmitting select scene images when it is determined that the scene image has sufficiently changed, etc.

The information gathered by device 100 or 138 can be continuously streamed to server system 160 in real-time. Thus, device 100 or 138 will track a particular item so long as the user continues to look at it. However, if the user changes his gaze (decision block 435) to focus on another item within his external scene, then on-board computing system 118 will commence tracking a new item (process block 440). Similarly, if the user rotates his head to look in a new direction, thereby changing his external scene (decision block 445), then process 400 continuously re-executes.

FIGS. 5A-D are flow charts illustrating server side processing for gaze tracking, in accordance with an embodiment. Each of process 500, 501, 502, and 503 may be executed by server system 160 illustrated in FIG. 3. The order in which some or all of the process blocks appear in each of processes 500, 501, 502, and 503 should not be deemed limiting. Rather, one of ordinary skill in the art having the benefit of the present disclosure will understand that some of the process blocks may be executed in a variety of orders not illustrated or even in parallel. Furthermore, processes 500, 501, 502, and 503 may all be continuously and concurrently executed by server system 160.

Figure 5A:
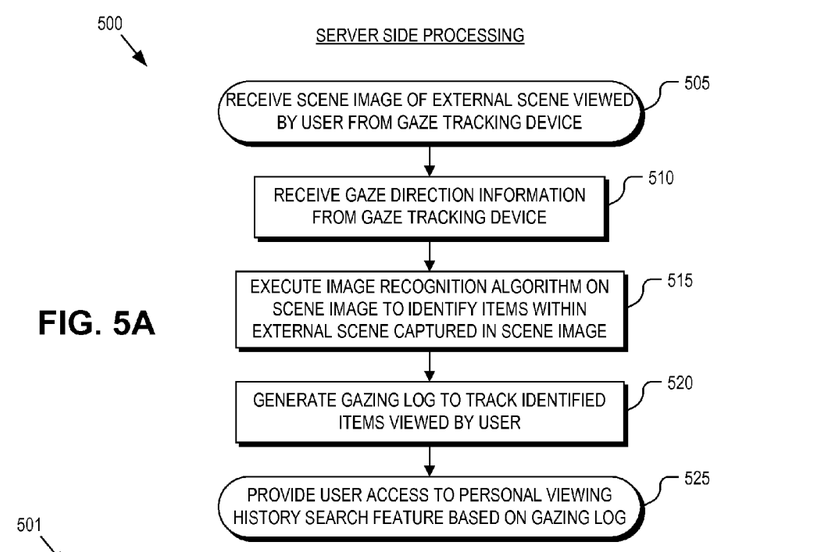
FIGS. 5A-D are flow charts illustrating server side processing for gaze tracking, in accordance with an embodiment.

Referring first FIG. 5A, in a process block 505, server system 160 receives a scene image from a gaze tracking device, such as device 100 or 138. The scene image is an image of the external scene viewed by the user while wearing the gaze tracking device. In one embodiment, scene images are continuously received from a given gaze tracking device in real-time while the user is wearing the device. In a process block 510, the gaze direction information is received from the gaze tracking device. The gaze direction information may be continuously received in real-time from the gaze tracking device. A new set of gaze tracking information may be received with each scene image or the gaze direction information may otherwise be keyed (e.g., time keyed, sequence keyed, etc.) to the continuous stream of scene images received from the gaze tracking device.

In a process block 515, server system 160 executes an image recognition algorithm on the scene image to identify item(s) within the user's external scene. In one embodiment, the image recognition is executed on just the item that the user is deemed to be directly looking at as determined by the gaze direction information. In another embodiment, the image recognition algorithm is executed on multiple items in the vicinity of where the user is gazing as determined by the gaze direction information. In yet another embodiment, the image recognition algorithm is executed on all items within the captured scene image that are amenable to visual searching.

If the visual search(es) result in an identifiable item(s), then each identified item is logged as an entry into the user's gazing log 175 (process block 520). Thus, gazing log 175 may include a listing of identified items, as identified by the image recognition algorithm, seen by the user while wearing the gaze tracking device. Each identified item within gazing log 175 may be indexed with additional information, such as, whether the user looked directly at the identified item per the gaze direction information, whether the identified item merely entered the user's peripheral view per the gaze direction information, how long the user looked directly at the identified item or how long the identified item was within the user's view, when (date & time) the user viewed the identified item, etc. In one embodiment, the indication of whether the user looked directly at an identified item is determined based upon both the gaze direction information and whether the user looked directly at the identified item for a threshold period of time to filter out glancing views. In one embodiment, each identified item may even be indexed along with location information (e.g., GPS position information) if the gaze tracking device is equipped with a GPS receiver. Of course, position information may also be acquired from local cell towers or WiFi hot spot locations at the time that the gaze tracking device transmits the scene images. Gazing log 175 may be generated and stored locally at server system 160 or archived into a database 170.

Once gazing log 170 begins to be populated with identified items viewed (either directly or peripherally) by the user, server system 160 may provide the user with access to a personal viewing history search feature (process block 525). In other words, the user may submit personal viewing history queries to server system 160. For example, the user may query whether he has seen a particular item in the past and if so, when, where, and how often. The personal viewing history search feature may provide the user with insight into his decision making processes. As an example, the user may find himself craving a particular food type or restaurant. By searching his gazing log, the user can see whether he has been the subject of recent advertisements for the food type or restaurant. The personal viewing history search feature may be used to view a list of historical influences by advertisers and provides the user with insight into their own decision making processes when making purchasing decisions.

Figure 5B:
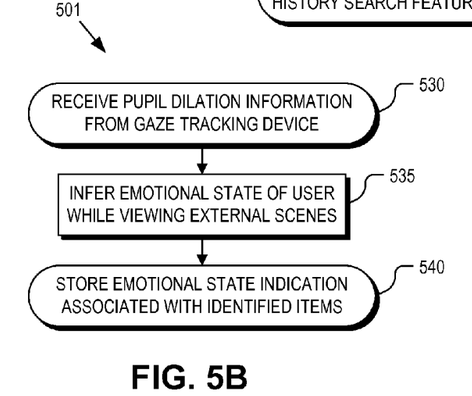

Turning to FIG. 5B, process 501 describes an emotional state tracking feature that may be implemented by server system 160, in accordance with an embodiment. In addition to gaze direction information, the eye images acquired by gaze tracking camera 121 can be analyzed for pupil dilation information. Pupil dilation can be correlated with emotional states, (e.g., surprise, interest, etc.). In one embodiment, onboard computing system 118 can analyze the eye images to determine pupil dilation and then generate pupil dilation information. This pupil dilation information can then be transmitted from the gaze tracking device and received at server system 160 (process block 530) along with the scene images and the gaze direction information. As with the gaze direction information, the pupil dilation information can be generated in real-time and keyed to the real-time scene images. In process block 535, server system 160 can infer one or more emotional states of the user while the user views an identified item within his external scene based on the pupil dilation information. In a process block 540, an emotional state indication may be included with entries in gazing log 175 indexed to the identified item viewed while the associated pupil dilation information was gathered.

Figure 5C:
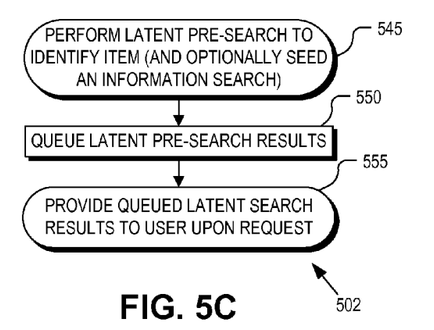

Turning to FIG. 5C, process 502 describes a latent search feature that may be implemented by server system 160, in accordance with an embodiment. As server system 160 receives scene images (e.g., process block 505 in FIG. 5A) from the gaze tracking device, it can execute the image recognition algorithm on all identifiable items within the scene image, as opposed to just the item upon which the user has directly fixed his gaze. In other words, server system 160 can perform visual searches on identifiable items within the user's peripheral view. Because the user may not have consciously noticed these items yet, the visual search of these items is referred to as a latent pre-search. Items in the user's peripheral view can then be used to seed latent pre-searches (process block 545) regardless of whether the user ultimately looks directly at a given item or not. The results of these latent pre-searches can be queued (process block 550). The queued latent search results can then be quickly accessed should the user look directly at the identified item and/or upon user request (process block 555). For example, when a user looks directly at an identified item being tracked by the system, the user may trigger an information search (e.g., Wikipedia search, Google search, etc.) to obtain general or specific background information on the identified item being tracked by signaling with a particular eye gesture or via finger-operable touch pads 124, 126 on device 100. The information search results can then be quickly served up to the user in the heads-up display (e.g., lens elements 110 and 112). Thus, latent pre-searching can improve visual searching to identify an item by triggering the visual search when it first enters the user's peripheral view before it reaches his direct gaze and speed up potential informational searches on identified items submitted by the user. In one embodiment, once a latent pre-search has identified a particular item, the informational search may also be automatically triggered as a latent pre-search and the informational results also queued for quick, on-demand user retrieval.

Figure 5D:
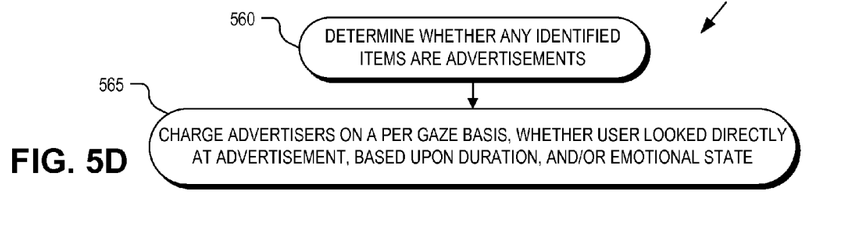

Turning to FIG. 5D, process 503 describes a pay per gaze advertising feature that may be implemented by server system 160, in accordance with an embodiment. After server system 160 executes the image recognition algorithm to identify items within the received scene images (e.g., process block 515 in FIG. 5A), server system 160 can then determine whether any of the identified items are advertisements (process block 560). In one embodiment, server system 160 may compare an identified item against a list of advertisers or advertising campaigns to see if the advertisement is registered for pay per gaze billing. Under a pay per gaze advertising scheme, advertisers are charged based upon whether a user actually viewed their advertisement (process block 565). Pay per gaze advertising need not be limited to on-line advertisements, but rather can be extended to conventional advertisement media including billboards, magazines, newspapers, and other forms of conventional print media. Thus, the gaze tracking system described herein offers a mechanism to track and bill offline advertisements in the manner similar to popular online advertisement schemes. Additional feature of a pay per gaze advertising scheme may include setting billing thresholds or scaling billing fees dependent upon whether the user looked directly at a given advertisement item, viewed the given advertisement item for one or more specified durations, and/or the inferred emotional state of the user while viewing a particular advertisement. Furthermore, the inferred emotional state information can be provided to an advertiser (perhaps for a premium fee) so that the advertiser can gauge the success of their advertising campaign. For example, if the advertiser desires to generate a shocking advertisement to get noticed or a thought provoking advertisement, then the inferred emotional state information and/or the gazing duration may be valuable metrics to determine the success of the campaign with real-world consumers.

Any of the metrics gathered by gaze tracking schemes described above may be accumulated across many users to create batched gaze tracking information. Analytical information (e.g., gazing statistics on a per user, per item, per advertisement) may then be generated based upon the batched gaze tracking information and provided to advertisers for a premium fee. The analytical information may be helpful for advertisers to refine and improve their advertisements. For example, advertisers may be interested in which specific advertisements tend to draw and hold a user's gaze and the type (e.g., emotional gaze) or intensity of their gaze based upon the pupil dilation information.

To protect individual privacy, personal identifying data may be removed from the data and provided to the advertisers as anonymous analytics. In one embodiment, users may be given opt-in or opt-out privileges to control the type of data being gathered, when the data is being gathered, or how the gathered data may be used or with whom it may be shared. Furthermore, individually identifying data maybe encrypted for communication between device 138 and server system 160 to further protect individual privacy.

Embodiments of the present disclosure are not limited accumulating analytical feedback information on advertisements. Rather, the gaze tracking schemes may further be used to test virtual user interfaces ("UI") to determine which on-screen elements draw the user eye, which elements distract, and generally gather gazing feedback information to refine and improve the user experience. This UI testing scheme may be extends to testing other interfaces, such automobile dashboards, flight controls, etc.

Figure 6:
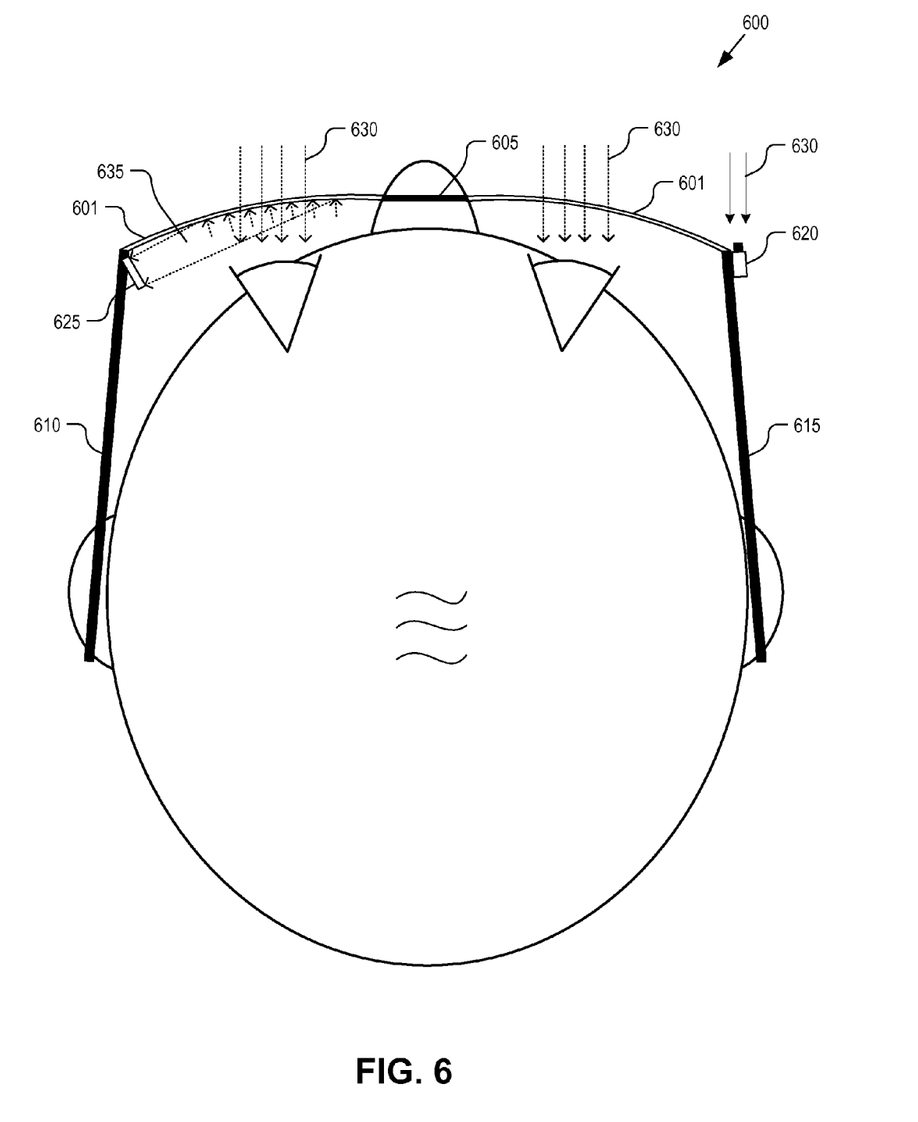
FIG. 6 is a top view illustrating another embodiment of a head mounted gaze tracking device.

FIG. 6 is a top view illustrating a head mounted gaze tracking device 600, in accordance with an embodiment. Device 600 represent one possible implementation of head mounted gaze tracking device 100 illustrated in FIGS. 1 and 2. The illustrated embodiment of device 600 includes two partially reflective and partially transparent lens elements

601, and a frame assembly including a nose bridge 605, left side-arm 610, right side-arm 615, scene camera 620, and gaze tracking camera 625. In this embodiment, lens elements 601 include an array of reflective elements that permit external light 630 to pass through lens elements 601 so that the user can perceive the external scene while reflecting an eye image 635 to gaze tracking camera 625.

Figure 7:
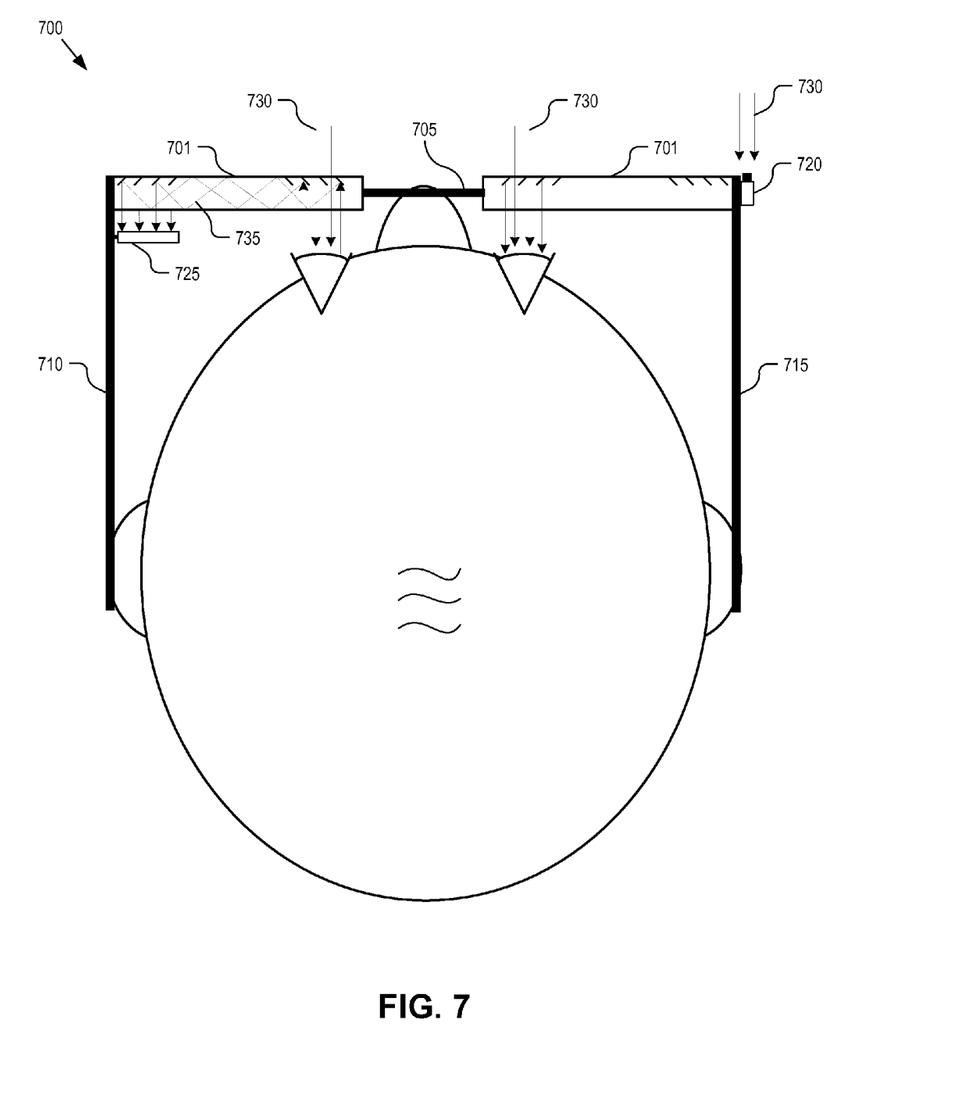
FIG. 7 is a top view illustrating yet another embodiment of a head mounted gaze tracking device.

FIG. 7 is a top view illustrating a head mounted gaze tracking device 700, in accordance with an embodiment. Device 700 represent another possible implementation of head mounted gaze tracking device 100 illustrated in FIGS. 1 and 2. The illustrated embodiment of device 700 includes two partially reflective and partially transparent lens elements 701, and a frame assembly including a nose bridge 705, left side-arm 710, right side-arm 715, scene camera 720, and gaze tracking camera 725. In this embodiment, lens elements 701 are waveguides that include an array of reflective elements disposed in or on the waveguide, which permit external light 730 to pass through a portion of the waveguide so that the user can perceive the external scene while reflecting an eye image 735 to gaze tracking camera 725. The waveguide structures of the lens elements 701 guide the reflected light of eye image 735 into gaze tracking camera 725.

The processes explained above are described in terms of computer software and hardware. The techniques described may constitute machine-executable instructions embodied within a tangible machine (e.g., computer) readable storage medium, that when executed by a machine will cause the machine to perform the operations described. Additionally, the processes may be embodied within hardware, such as an application specific integrated circuit ("ASIC") or the like.

A tangible machine-readable storage medium includes any mechanism that provides (i.e., stores) information in a form accessible by a machine (e.g., a computer, network device, personal digital assistant, manufacturing tool, any device with a set of one or more processors, etc.). For example, a tangible machine-readable storage medium includes one or more recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. A method comprising:
    receiving scene images from a head mounted gaze tracking device capturing external scenes viewed by a user wearing the head mounted device, the scene images received at a server via a network;
    receiving gaze direction information from the head mounted gaze tracking device along with the scene images, the gaze direction information indicating where in the external scenes the user was gazing when viewing the external scenes, the gaze direction information received at the server via the network;
    executing an image recognition algorithm on the scene images to identify items within the external scenes viewed by the user;
    generating a gazing log tracking the identified items viewed by the user;
    performing latent pre-searches on at least a portion of the items viewed by the user to generate latent search results, wherein the latent pre-searches are automatically triggered while the associated items are in the user's peripheral view and without affirmative requests on a per search basis by the user; and
    caching the latent search results.

2. The method of claim 1, wherein generating the gazing log further comprises storing an indication of whether the user looked directly at the identified items based at least in part upon the gaze direction information.

3. The method of claim 2, wherein the user is deemed to have looked directly at a given identified item if a position of the given identified item within a given scene image correlates to the gaze direction information associated with the given scene image and if the user looked directly at the given identified item for a threshold period of time.

4. The method of claim 2, wherein generating the gazing log further comprises storing an indication of how long and when the user looked at one or more of the identified items based upon the gaze direction information.

5. The method of claim 1, further comprising:
    receiving pupil dilation information from the head mounted gaze tracking device along with the scene images, the pupil dilation information indicating a pupil dilation of the user while viewing the external scenes, the pupil dilation information received at the server via the network.

6. The method of claim 5, further comprising:
    inferring an emotional state of the user while viewing the external scenes based at least in part upon the pupil dilation information; and
    storing an emotional state indication associated with one or more of the identified items.

7. The method of claim 1, further comprising:
    determining which, if any, of the identified items within the external scenes viewed by the user are advertisements; and
    charging advertisers associated with the advertisements based at least in part on a per gaze basis.

8. The method of claim 7, wherein charging the advertisers further comprises charging a given advertiser associated with a given advertisement based at least in part upon whether the user looked directly at the given advertisement as determined by the gaze direction information and how long the user looked at the given advertisement.

9. The method of claim 1, further comprising:
    determining which, if any, of the identified items within the external scenes viewed by the user are advertisements; and
    charging advertisers for analytical information generated based upon the gazing direction information.

10. The method of claim 9, further comprising:
    combining the gazing direction information acquired from the user wearing the head mounted device with other gazing direction information acquired from other users wearing other head mounted devices to generate batched information; and
    charging advertisers for the analytical information generated based upon the batched information.

11. The method of claim 10, wherein the analytical information includes the tendency of a given advertisement to draw user gazes or to hold the user gazes.

12. The method of claim 10, wherein the analytical information includes the tendency of a given advertisement to evoke an emotional response.

13. The method of claim 1, further comprising:
providing selected ones of the cached latent search results to the user upon request.

14. The method of claim 2, further comprising:
providing the user access to a personally viewing history search feature; and
searching the gazing log upon receiving a viewing history search request from the user.

15. The method of claim 14, wherein the viewing history search feature provides the user with a list of historical influences by advertisements.

16. The method of claim 1, wherein the head mounted gaze tracking device comprises eyeglasses including side-arms that engage ears of the user, a nose bridge that engages a nose of the user, and lenses through which the user views the external scenes,
wherein the scene images are captured in real-time while the user views the external scenes with at least one forward facing scene camera disposed on the eyeglasses,
wherein the gaze direction information is generated based upon eye images of at least one eye of the user captured in real-time while the user views the external scenes with at least one gaze tracking camera disposed on the eyeglasses.

17. The method of claim 16, wherein the gaze direction information is captured based upon the eye images captured with the at least one gaze tracking camera being substantially forward facing and disposed on at least one of the side-arms of the eyeglasses, the eye images captured based upon reflections off of at least one of the lenses through which the user perceives the external scene.

18. A tangible machine-readable storage medium that provides instructions that, when executed by a machine, will cause the machine to perform operations comprising:
receiving scene images from a head mounted gaze tracking device capturing external scenes viewed by a user wearing the head mounted device, the scene images received at a server via a network;
receiving gaze direction information from the head mounted gaze tracking device along with the scene images, the gaze direction information indicating where in the external scenes the user was gazing when viewing the external scenes, the gaze direction information received at the server via the network;
executing an image recognition algorithm on the scene images to identify items within the external scenes viewed by the user;
generating a gazing log tracking the identified items viewed by the user;
performing latent pre-searches on at least a portion of the items viewed by the user to generate latent search results, wherein the latent pre-searches are automatically triggered while the associated items are in the user's peripheral view and without affirmative requests on a per search basis by the user; and
caching the latent search results.

19. The tangible machine-readable storage medium of claim 18, wherein generating the gazing log further comprises storing an indication of whether the user looked directly at the identified items based at least in part upon the gaze direction information.

20. The tangible machine-readable storage medium of claim 19, wherein the user is deemed to have looked directly at a given identified item if a position of the given identified item within a given scene image correlates to the gaze direction information associated with the given scene image and if the user looked directly at the given identified item for a threshold period of time.

21. The tangible machine-readable medium of claim 18, further providing instructions that, when executed by the machine, will cause the machine to perform further operations, comprising:
receiving pupil dilation information from the head mounted gaze tracking device along with the scene images, the pupil dilation information indicating a pupil dilation of the user while viewing the external scenes, the pupil dilation information received at the server via the network.

22. The tangible machine-readable medium of claim 21, further providing instructions that, when executed by the machine, will cause the machine to perform further operations, comprising:
inferring emotional state of the user while viewing the external scenes based at least in part upon the pupil dilation information; and
storing an emotional state indication associated with one or more of the identified items.

23. The tangible machine-readable medium of claim 18, further providing instructions that, when executed by the machine, will cause the machine to perform further operations, comprising:
determining which, if any, of the identified items within the external scenes viewed by the user are advertisements; and
charging advertisers associated with the advertisements based at least in part on a per gaze basis and whether the user looked directly at the given advertisement as determined by the gaze direction information and how long the user looked at the given advertisement.

24. The tangible machine-readable medium of claim 18, further providing instructions that, when executed by the machine, will cause the machine to perform further operations, comprising:
providing selected ones of the cached latent search results to the user upon request.

25. The tangible machine-readable medium of claim 18, further providing instructions that, when executed by the machine, will cause the machine to perform further operations, comprising:
providing the user access to a personally viewing history search feature; and
searching the gazing log upon receiving a viewing history search request from the user.

* * * * *